US012766203B2

(12) United States Patent
Imai et al.

(10) Patent No.: US 12,766,203 B2
(45) Date of Patent: Oct. 20, 2026

(54) METHOD FOR PRODUCING RADIOACTIVE ZIRCONIUM COMPLEX

(71) Applicant: NIHON MEDI-PHYSICS CO., LTD., Tokyo (JP)

(72) Inventors: Tomoyuki Imai, Tokyo (JP); Hiroaki Ichikawa, Tokyo (JP); Satoshi Kishimoto, Tokyo (JP); Akihiro Izawa, Tokyo (JP)

(73) Assignee: NIHON MEDI-PHYSICS CO., LTD., Tokyo (JP)

(*) Notice: Subject to any disclaimer, the term of this patent is extended or adjusted under 35 U.S.C. 154(b) by 656 days.

(21) Appl. No.: 18/249,753

(22) PCT Filed: Oct. 14, 2021

(86) PCT No.: PCT/JP2021/038138
§ 371 (c)(1),
(2) Date: Apr. 20, 2023

(87) PCT Pub. No.: WO2022/085571
PCT Pub. Date: Apr. 28, 2022

(65) Prior Publication Data

US 2023/0390426 A1 Dec. 7, 2023

(30) Foreign Application Priority Data

Oct. 22, 2020 (JP) ................................ 2020-177567

(51) Int. Cl.
*A61K 51/10* (2006.01)
*A61K 51/04* (2006.01)
*A61K 51/08* (2006.01)

(52) U.S. Cl.
CPC ...... *A61K 51/1096* (2013.01); *A61K 51/0491* (2013.01); *A61K 51/088* (2013.01)

(58) Field of Classification Search
None
See application file for complete search history.

(56) References Cited

U.S. PATENT DOCUMENTS

| | | | | |
|---|---|---|---|---|
| 2002/0122768 | A1 | 9/2002 | Liu et al. | |
| 2005/0233955 | A1* | 10/2005 | Taylor | A61P 25/16 514/8.4 |
| 2007/0092940 | A1 | 4/2007 | Eigenbrot et al. | |
| 2009/0005595 | A1* | 1/2009 | Janssen | A61K 47/12 564/237 |
| 2015/0299133 | A1 | 10/2015 | Osterkamp et al. | |
| 2016/0199520 | A1 | 7/2016 | Fukunaga et al. | |
| 2019/0038785 | A1 | 2/2019 | Wadas et al. | |
| 2019/0192660 | A1* | 6/2019 | Romoren | C01B 9/08 |
| 2020/0181196 | A1 | 6/2020 | Ito et al. | |

FOREIGN PATENT DOCUMENTS

| | | | | |
|---|---|---|---|---|
| JP | 2016501238 | A | 1/2016 | |
| KR | 20150115359 | A | 10/2015 | |
| RU | 2562862 | C2 * | 9/2015 | C07C 259/06 |
| WO | 0204030 | A2 | 1/2002 | |
| WO | 2015046278 | A1 | 4/2015 | |
| WO | 2017161356 | A1 | 9/2017 | |
| WO | WO-2019125982 | A1 * | 6/2019 | C07K 16/3069 |

OTHER PUBLICATIONS

Google Patents. English Translation of RU2562862C2. https://patents.google.com/patent/RU2562862C2/en?oq=RU+2562862+ accessed by examiner on Nov. 5, 2025, originally published in Russian on Sep. 10, 2015, 81 printed pages. (Year: 2015).*

Jonathan R. Dilworth and Sofia I. Pascu. "The chemistry of PET imaging with zirconium-89." Chemical Society Reviews, vol. 47, 2018, pp. 2554-2571. (Year: 2018).*

Office Action issued on May 7, 2025, by the Japanese Patent Office in corresponding Japanese Application No. 2022-557464, and English translation of the Office Action (11 pages).

Office Action issued Nov. 30, 2023, in corresponding EA Application No. 202391094, and an English translation of the Office Action.

Office Action issued on Mar. 16, 2025, by the State Intellectual Property Office of People's Republic of China in corresponding Chinese Application No. 202180072001.5, and English translation of the Office Action (15 pages).

International Search Report (PCT/ISA/210) with an English translation, and Written Opinion (PCT/ISA/237) mailed on Dec. 21, 2021, by the Japanese Patent Office as the International Searching Authority for International Application No. PCT/JP2021/038138. (9 pages).

Wei, Ling et al., "Preparation of clinical-grade $^{89}$Zr-panitumumab as a positron emission tomography biomarker for evaluating epidermal growth factor receptor-targeted therapy", J Labelled Comp Radiopharm., NIH Public Access, Jan. 2014, vol. 57, Issue 1, pp. 25-35. (22 pages).

Search Report and Written Opinion issued on Nov. 27, 2024, by Intellectual Property Office of Singapore in corresponding Singapore Application No. 11202303076Y (8 pages).

Office Action issued on Oct. 14, 2025, by the Intellectual Property Office of Singapore in corresponding SG Application No. 11202303076Y (4 pages).

(Continued)

*Primary Examiner* — Isaac Shomer
(74) *Attorney, Agent, or Firm* — Panitch Schwarze Belisario & Nadel LLP

(57) ABSTRACT

A method for producing a radioactive zirconium complex of the present invention includes a step of reacting a radioactive zirconium ion, a ligand compound containing DOTA or a DOTA derivative, and an additive such as hydroxybenzoic acid and a derivative thereof with one another in a reaction solution to form a radioactive zirconium complex. As the reaction solution, a reaction solution is used in which the amount of radioactivity of the radioactive zirconium ion is 60 MBq or more at the start of the reaction and the amount of radioactivity of the radioactive zirconium ion is 5 MBq or more per 1 nmol of the ligand compound at the start of the reaction.

14 Claims, No Drawings

(56) References Cited

OTHER PUBLICATIONS

Extended European Search Report issued on Sep. 4, 2024, in corresponding European Application No. 21882712.9 (10 pages).
Office Action issued on Aug. 20, 2024, in corresponding Eurasian Application No. 202391094, and an English translation of the Office Action (7 pages).
Office Action issued on Aug. 1, 2025, by the Taiwanese Intellectual Property Office in corresponding Taiwan Application No. 110138655, and English translation of the Office Action (10 pages).
Perk et al., "p-Isothiocyanatobenzyl-desferrioxamine: a new bifunctional chelate for facile radiolabeling of monoclonal antibodies with zirconium-89 for immuno-PET imaging," Eur. J. Nucl. Med. Mol. Imaging, vol. 37, pp. 250-259 (2010).
Office Action issued on Apr. 30, 2026, by the Korean Patent Office in corresponding KR Application No. 10-2023-7016882, and English translation of the Office Action (14 pages).

* cited by examiner

METHOD FOR PRODUCING RADIOACTIVE ZIRCONIUM COMPLEX

TECHNICAL FIELD

The present invention relates to a method for producing a radioactive zirconium complex.

BACKGROUND ART

For the purpose of use in reagents and diagnostic agents for detection of target molecules or pharmaceuticals for treatment of diseases, studies on the yield of a radioactive metal complex in which a ligand compound is coordinated to a radioactive metal have been conducted.

Patent Literatures 1 and 2 disclose that a Zr complex was formed in a liquid containing gentisic acid using radioactive zirconium and an antibody to which deferoxamine (DFO), which is a kind of ligand compound, has been bonded.

In addition, Non Patent Literature 1 discloses a method in which $^{89}Zr$, which is a radioactive metal, and an antibody to which DFO has been bonded are reacted with each other in a buffer solution containing gentisic acid and adjusted to a pH of about 7 to form a radioactive metal complex.

CITATION LIST

Patent Literatures

Patent Literature 1: US 2007/092940 A
Patent Literature 2: US 2020/181196 A

Non Patent Literature

Non Patent Literature 1: Wei et al, J Labelled Comp Radiopharm. 57(1): 25-35, 2014.

SUMMARY OF INVENTION

However, in Patent Literatures 1 and 2 and Non Patent Literature 1, no condition for complex formation between DOTA and a radioactive zirconium ion has been studied. In addition, it has become clear from the findings of the present inventors that under any conditions disclosed in these literatures, complex formation between DOTA and a radioactive zirconium ion does not proceed well, and a sufficient labeling index cannot be achieved in some cases. In particular, reaction conditions that can realize a high labeling index when the amount of radioactivity prepared is increased have been desired.

Therefore, the present invention relates to a method for producing a radioactive zirconium complex that can realize a high labeling index in a reaction with a ligand compound containing DOTA or a DOTA derivative.

The present invention provides a method for producing a radioactive zirconium complex, including a step of reacting a radioactive zirconium ion and a ligand compound represented by Formula (1) below in a reaction solution to form a radioactive zirconium complex, wherein the reaction solution has:

an amount of radioactivity of the radioactive zirconium ion of 60 MBq or more at the start of the reaction; and an amount of radioactivity of the radioactive zirconium ion of 5 MBq or more per 1 nmol of the ligand compound at the start of the reaction, and the step is performed in the presence of an additive represented by Formula (2) below or a salt thereof.

(1)

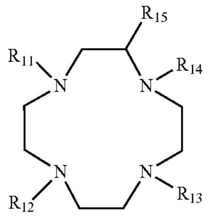

wherein $R_{11}$, $R_{12}$, and $R_{13}$ each independently represent a $-(CH_2)_pCOOH$ group, a $-(CH_2)_pC_5H_4N$ group, a $-(CH_2)_pPO_3H_2$ group, or a $-(CH_2)_pCONH_2$ group, one of $R_{14}$ and $R_{15}$ represents a hydrogen atom, a $-(CH_2)_pCOOH$ group, a $-(CH_2)_pC_5H_4N$ group, a $-(CH_2)_pPO_3H_2$ group, a $-(CH_2)_pCONH_2$ group, or a $-(CHCOOH)(CH_2)_pCOOH$ group, the other one is a $-(CH_2)_pCOOH$ group, a $-(CH_2)_pC_5H_4N$ group, a $-(CH_2)_pPO_3H_2$ group, a $-(CH_2)_pCONH_2$ group, a reactive atomic group to be linked to a targeting agent, or a group linked to the targeting agent, and p each independently represents an integer of 0 or more and 3 or less;

(2)

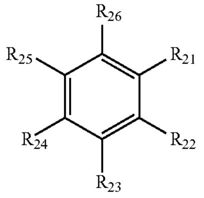

wherein $R_{21}$ represents a $-COOH$ group, a $-CH_2COOH$ group, a $-CH_2OH$ group, a $-COOR_{28}$ group, a $-CONH_2$, group or a $-CONHR_{28}$ group, 1 or more and 3 or less groups of $R_{22}$ to $R_{26}$ represent hydroxy groups, other groups represent hydrogen atoms, and $R_{28}$ represents a substituted or unsubstituted alkyl, a substituted or unsubstituted aryl, or a substituted or unsubstituted alkylaryl.

DESCRIPTION OF EMBODIMENT

Hereinafter, a method for producing a radioactive zirconium complex of the present invention will be described on the basis of a preferable embodiment thereof. The production method of the present invention includes a step (hereinafter also simply referred to as a "step") of causing a reaction in a reaction solution containing a radioactive zirconium ion as a radioactive metal ion, a ligand compound represented by Formula (1) described later, and an additive represented by Formula (2) described later or a salt thereof to coordinate the radioactive zirconium ion to the ligand compound, thereby forming a radioactive zirconium complex.

The radioactive zirconium complex obtained through the present step is a compound in which a radioactive zirconium atom is bonded to the ligand compound by a combination of a covalent bond, an ionic bond, and the like in addition to a coordinate bond. The radioactive zirconium complex also includes a compound to which a reactive atomic group or a targeting agent described later is further bonded.

In the present specification, complexing the radioactive zirconium ion with the ligand compound and labeling the ligand compound with the radioactive zirconium ion are synonymous, and complexing efficiency and a labeling index are synonymous.

In the following description, unless otherwise specified, “radioactive zirconium” is simply referred to as “radioactive Zr”.

From the viewpoint of increasing the labeling index, the radioactive Zr used in the present step is preferably used in the form of a compound capable of being ionized in water, more preferably used in the form of a Zr ion (hereinafter these forms are also collectively referred to as a “radioactive Zr source”). As the radioactive Zr source, for example, a radioactive Zr ion-containing solution in which radioactive Zr ions are dissolved or dispersed in a solvent mainly composed of water can be used.

The nuclide of radioactive Zr is preferably $^{89}Zr$. $^{89}Zr$ is a $\beta^+$-ray decay nuclide and is an electron-capturing decay nuclide. $^{89}Zr$ can be produced, for example, by a nuclear reaction of $^{89}Y(p,n)^{89}Zr$ using a cyclotron. Specifically, a solution obtained by dissolving a $^{89}Y$ target after proton irradiation using an acid is passed through a column cartridge or the like supporting a collector capable of adsorbing $^{89}Zr$. Thereafter, the column cartridge is washed with a solvent such as water, and then an oxalic acid aqueous solution is passed through the column cartridge, so that $^{89}Zr$ ions can be eluted and collected as a solution.

The ligand compound used in the present step has a structure represented by Formula (1) below.

(1)

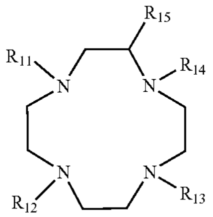

In Formula (1), $R_{11}$, $R_{12}$, and $R_{13}$ each independently represent a $-(CH_2)_pCOOH$ group, a $-(CH_2)_pC_5H_4N$ group, a $-(CH_2)_pPO_3H_2$ group, or a $-(CH_2)_pCONH_2$ group.

p is each independently an integer of 0 or more and 3 or less.

In Formula (1), one of $R_{14}$ and $R_{15}$ represents a hydrogen atom, a $-(CH_2)_pCOOH$ group, a $-(CH_2)_pC_5H_4N$ group, a $-(CH_2)_pPO_3H_2$ group, a $-(CH_2)_pCONH_2$ group, or a $-(CHCOOH)(CH_2)_pCOOH$ group.

In Formula (1), the other one of $R_{14}$ and $R_{15}$ represents a $-(CH_2)_pCOOH$ group, a $-(CH_2)_pC_5H_4N$ group, a $-(CH_2)_pPO_3H_2$ group, a $-(CH_2)_pCONH_2$ group, a reactive atomic group to be linked to the targeting agent, or a group linked to the targeting agent.

p each independently represents an integer of 0 or more and 3 or less.

Details of the targeting agent and the reactive atomic group to be linked to the targeting agent or the group linked to the targeting agent will be described later.

More specifically, the ligand compound used in the present step more preferably contains one compound shown below or a structure derived from the compound. The ligand compound used in the present step is preferably water-soluble.

DOTA(1,4,7,10-Tetraazacyclododecane-1,4,7,10-tetraacetic acid)

DOTMA((1R,4R,7R,10R)-α,α',α'',α'''-tetramethyl-1,4,7,10-tetraazacyclododecane-1,4,7,10-tetraacetic acid)

DOTAM(1,4,7,10-tetrakis(carbamoylmethyl)-1,4,7,10-tetraazacyclododecane)

DOTA-GA(α-(2-Carboxyethyl)-1,4,7,10-tetraazacyclododecane-1,4,7,10-tetraacetic acid)

DOTP(((1,4,7,10-Tetraazacyclododecane-1,4,7,10-tetrayl)tetrakis(methylene))tetraphosphonicacid)

DOTMP(1,4,7,10-Tetraazacyclododecane-1,4,7,10-tetrakis(methylenephosphonic acid))

DOTA-4AMP(1,4,7,10-tetraazacyclododecane-1,4,7,10-tetrakis(acetamidomethylenephosphonic acid)

DO2P(Tetraazacyclododecane dimethanephosphonic acid)

The additive used in the present step has a structure represented by Formula (2) below or a salt thereof. The additive may be used singly or in combination of two or more kinds thereof. By including such an additive in the reaction solution, the labeling index can be increased even when the amount of radioactivity (amount of radioactivity prepared) at the start of the reaction is increased for the purpose of commercial production or the like. As a result, the yield of the target radioactive Zr complex can be increased.

(2)

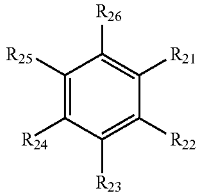

In Formula (2), $R_{21}$ represents a $-COOH$ group, a $-CH_2COOH$ group, a $-CH_2OH$ group, a $-COOR_{28}$ group, a $-CONH_2$ group, or a $-CONHR_{28}$ group.

In Formula (2), one or more and three or less groups among $R_{22}$ to $R_{26}$ are hydroxy groups (the OH form), and the other groups are hydrogen atoms.

In Formula (2), when $R_{21}$ includes $R_{28}$, $R_{28}$ is a substituted or unsubstituted alkyl, a substituted or unsubstituted aryl, or a substituted or unsubstituted alkylaryl. $R_{28}$ may be linear or branched and may be saturated or unsaturated.

The total carbon number of $R_{28}$ is preferably 1 or more and 10 or less, more preferably 1 or more and 8 or less.

When the additive represented by Formula (2) is used as a salt, examples of the counter ion include ions of alkali metals such as sodium and potassium, cations such as primary to quaternary ammonium such as ammonium and a tetramethylammonium salt, and anions of halogens and the like such as chlorine.

Examples of the structure of the additive represented by Formula (2) include, but are not limited to, structures represented by any of Formulas (2a) to (2g) below.

(2a)

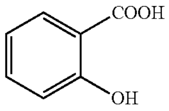

(2b)

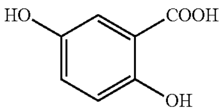

(2c)

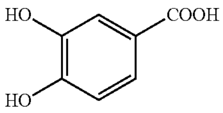

(2d)

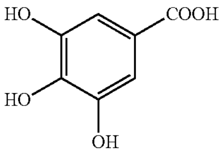

(2e)

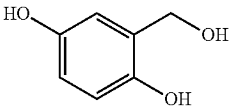

(2f)

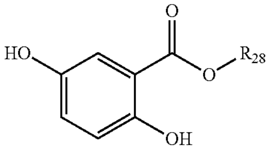

(2g)

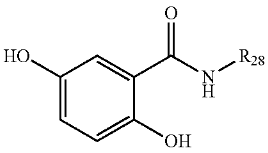

An embodiment of the additive represented by Formula (2) is an embodiment in which $R_{21}$ is a carboxy group (the COOH form). That is, the additive in the present embodiment is hydroxybenzoic acid.

Examples of the hydroxybenzoic acid represented by Formula (2) include monohydroxybenzoic acid, dihydroxybenzoic acid, and trihydroxybenzoic acid.

Examples of monohydroxybenzoic acid include the following forms.

2-Hydroxybenzoic acid (salicylic acid): In Formula (2), $R_{21}$ is a —COOH, $R_{22}$ is OH, and all of $R_{23}$ to $R_{26}$ are hydrogen atoms. This embodiment corresponds to Formula (2a).

3-Hydroxybenzoic acid: In Formula (2), $R_{21}$ is —COOH, $R_{23}$ is —OH, and all of $R_{22}$ and $R_{24}$ to $R_{26}$ are hydrogen atoms.

4-Hydroxybenzoic acid: In Formula (2), $R_{21}$ is a —COOH, $R_{24}$ is —OH, and all of $R_{22}$, $R_{23}$, $R_{25}$, and $R_{26}$ are hydrogen atoms.

Examples of dihydroxybenzoic acid include the following forms.

2,3-Dihydroxybenzoic acid (2-pyrocatechuic acid): In Formula (2), $R_{21}$ is —COOH, both of $R_{22}$ and $R_{23}$ are —OH, and all of $R_{24}$ to $R_{26}$ are hydrogen atoms.

2,4-Dihydroxybenzoic acid (β-resorcylic acid): In Formula (2), $R_{21}$ is —COOH, both of $R_{22}$ and $R_{24}$ are —OH, and all of $R_{23}$, $R_{25}$, and $R_{26}$ are hydrogen atoms.

2,5-Dihydroxybenzoic acid (gentisic acid): In Formula (2), $R_{21}$ is —COOH, both of $R_{22}$ and $R_{25}$ are —OH, and all of $R_{23}$, $R_{24}$, and $R_{26}$ are hydrogen atoms. This embodiment corresponds to Formula (2b).

2,6-Dihydroxybenzoic acid (γ-resorcylic acid): In Formula (2), $R_{21}$ is —COOH, both of $R_{22}$ and $R_{26}$ are —OH, and all of $R_{23}$, $R_{24}$, and $R_{25}$ are hydrogen atoms.

3,4-Dihydroxybenzoic acid (protocatechuic acid): In Formula (2), $R_{21}$ is —COOH, both of $R_{23}$ and $R_{24}$ are —OH, and all of $R_{22}$, $R_{25}$, and $R_{26}$ are hydrogen atoms. This embodiment corresponds to Formula (2c).

3,5-Dihydroxybenzoic acid (α-resorcylic acid): In Formula (2), $R_{21}$ is —COOH, both of $R_{23}$ and $R_{25}$ are —OH, and all of $R_{22}$, $R_{24}$, and $R_{26}$ are hydrogen atoms.

Examples of trihydroxybenzoic acid include, but are not limited to, the following forms.

3,4,5-Trihydroxybenzoic acid (gallic acid): In Formula (2), $R_{21}$ is —COOH, all of $R_{23}$ to $R_{25}$ are —OH, and both of $R_{22}$ and $R_{26}$ are hydrogen atoms. This embodiment corresponds to Formula (2d).

2,4,6-Trihydroxybenzoic acid: In Formula (2), $R_{21}$ is —COOH, all of $R_{22}$, $R_{24}$, and $R_{26}$ are —OH, and both of $R_{23}$ and $R_{25}$ are hydrogen atoms.

Another embodiment of the additive represented by Formula (2) is an embodiment in which $R_{21}$ is —$CH_2OH$ group, —$COOR_{28}$ group, or —$CONHR_{28}$ group. Examples of compounds corresponding to this embodiment include, but are not limited to, the following forms.

Gentisyl alcohol: In Formula (2), $R_{21}$ is —$CH_2OH$ group, both of $R_{22}$ and $R_{25}$ are —OH, and all of $R_{23}$, $R_{24}$, and $R_{26}$ are hydrogen atoms. This embodiment corresponds to Formula (2e).

An alkyl ester of gentisic acid: In Formula (2), $R_{21}$ is —$COOR_{28}$ group, both of $R_{22}$ and $R_{25}$ are —OH, all of $R_{23}$, $R_{24}$, and $R_{26}$ are hydrogen atoms, and $R_{28}$ is a saturated linear alkyl group having a carbon number of one or more and eight or less. This embodiment is one embodiment included in Formula (2f).

Gentisic acid ethanolamide: In Formula (2), $R_{21}$ is —$CONHR_{28}$ group, both of $R_{22}$ and $R_{25}$ are —OH, all of $R_{23}$, $R_{24}$, and $R_{26}$ are hydrogen atoms, and $R_{28}$ is —$CH_2$—$CH_2OH$ group. This embodiment is one embodiment included in Formula (2g).

Among them, from the viewpoint of reducing the decomposition of the ligand compound or the product by radioactivity to further increase the labeling index, as the additive, it is preferable to use a compound having a structure represented by any one of Formulas (2a) to (2g) or a salt thereof, it is more preferable to use a compound having a structure represented by any one of Formulas (2a) to (2d) or a salt thereof, and it is still more preferable to use a compound having a structure represented by Formula (2b) or a salt thereof. That is, the additive is more preferably salicylic acid, gentisic acid, protocatechuic acid, gallic acid, or a salt thereof, still more preferably gentisic acid or a salt thereof.

The reaction solution in the present step is an aqueous reaction solution further containing water in addition to the radioactive Zr source, the ligand compound, and the additive described above.

As the water, water commonly used in the present technical field can be employed, and for example, distilled water or ion-exchanged water can be used.

In the present step, the reaction solution is heated to cause the reaction, and one of the features is that the amount of radioactivity in the reaction solution and the ratio of the amount of radioactivity to the amount of the ligand compound at the start of the present step are set to predetermined values or more.

Specifically, as the amount of radioactivity in the reaction solution at the start of the reaction, the amount of radioactivity of the radioactive Zr ion is 60 MBq or more, preferably 100 MBq or more, more preferably 150 MBq or more.

In addition, as the ratio between the ligand compound and the amount of radioactivity in the reaction solution at the start of the reaction, the amount of radioactivity of the radioactive Zr ion per 1 nmol of the ligand compound is set to 5 MBq or more, preferably 10 MBq or more, more preferably 20 MBq or more. The upper limit is not particularly limited but is, for example, 10,000 MBq or less.

The upper limit of the amount of radioactivity in the reaction solution at the start of the reaction is not particularly limited as long as it is an amount of radioactivity that can be realized on a commercial production scale but can be, for example, 1,000 GBq or less.

In order to achieve such an amount of radioactivity in the reaction solution, for example, an oxalic acid solution containing radioactive Zr obtained as described above is passed through a column cartridge supporting an anion exchange resin, washing with water or the like is performed, and then an acidic solution is passed to perform elution from the column. Then, the product is heated to be dried and solidified under an inert gas flow. The operation can be performed by dissolving the dried solid containing radioactive Zr thus obtained using a desired liquid amount of an acid to appropriately adjust the radioactivity concentration.

By achieving the above-described amount of radioactivity in the reaction solution and the ratio between the amount of radioactivity and the amount of the ligand compound, for example, even when the production scale is increased for commercial production of a radiopharmaceutical composition containing a radioactive Zr complex as an active ingredient, a high labeling index can be achieved, and the yield increases accordingly. As a result, the production efficiency of the radioactive Zr complex can be increased.

In the present step, the order of addition of the radioactive Zr source, the ligand compound, and the additive is not limited as long as the labeling reaction of the ligand compound with the radioactive Zr ion can proceed, specifically, the complex formation between the radioactive Zr ion and the ligand compound can be performed, on condition that the relationship between the amount of radioactivity and the ratio of the amount of radioactivity to the amount of the ligand compound in the reaction solution described above is satisfied. For example, one of the radioactive Zr source and the ligand compound may be added to a reaction vessel already accommodating a mixed liquid in which a solvent such as water constituting the reaction solution and the additive are mixed, and then the other may be added and reacted. Alternatively, one of the radioactive Zr source and the ligand compound may be added to a solution obtained by dissolving the other in advance in a mixed liquid to cause the reaction. Alternatively, the radioactive Zr source, the ligand compound, and the additive may be simultaneously added to a reaction vessel already accommodating a solvent such as water to cause the reaction.

The reaction solution used in the present step may not contain an organic solvent, or an organic solvent may be added depending on the physical properties of the ligand compound and the additive. Examples of such an organic solvent include water-soluble organic solvents such as polar solvents such as protic solvents such as methanol and ethanol, and aprotic solvents such as acetonitrile, N,N-dimethylformamide, tetrahydrofuran, dimethyl sulfoxide, and acetone. By including such an organic solvent, even when poorly water-soluble substances are used as the ligand compound and the additive, the ligand compound and the additive can be sufficiently dissolved or dispersed in the solvent, and a high labeling index can be stably achieved.

The phrase "not contain an organic solvent" means that an organic solvent is not intentionally contained in the reaction solution, but inevitable mixing of an organic solvent in the reaction solution is acceptable.

The reaction conditions in the present step can be, for example, the following conditions.

As the reaction solution used in the present step, an aqueous solution containing water, the ligand compound, the additive, and the radioactive Zr source and containing an organic solvent added as necessary is used. At this time, the reaction solution is prepared so that the amount of radioactivity of the radioactive Zr ion in the reaction solution and the ratio between the amount of radioactivity and the amount of the ligand compound will satisfy the predetermined relationship described above.

The reaction pressure can be atmospheric pressure.

In the present step, from the viewpoint of achieving further improvement in labeling efficiency in a short production time, it is preferable to carry out the reaction by heating the reaction solution. The heating means applying heat from the outside of the reaction system such that the temperature of the reaction solution becomes higher than 25° C. on the basis of 25° C. As a method for applying heat from the outside of the reaction system, a known method can be appropriately used, and examples thereof include a water bath, an oil bath, a block heater, and a heating mantle.

In the case where the reaction solution is heated to carry out the reaction, the reaction solution is heated to a reaction temperature of preferably 30° C. or higher and 100° C. or lower, more preferably 50° C. or higher and 80° C. or lower, from the viewpoint of achieving both suppression of the decomposition of the ligand compound and further improvement of the labeling efficiency.

The reaction time is preferably 15 minutes or more and 150 minutes or less, more preferably 30 minutes or more and 120 minutes or less, on condition that the reaction temperature is as described above.

The amount of the reaction solution in the present step can be appropriately changed according to the production scale. From the viewpoint of practicality in the production process, 0.01 mL or more is practical at the start of the present step. The amount of the reaction solution is not particularly limited but is practically about 100 mL or less.

In the production method of the present invention including the step described above, since radioactive Zr and the ligand compound are easily dissolved in the reaction solution, the labeling reaction can uniformly proceed in the liquid phase. In addition to this, in the present step, the reaction is carried out by heating in a state where the additive having the above-described specific structure is present in the reaction system, whereby even in the case where the amount of radioactivity used at the start of the reaction in the present step is set to a value much higher than that in the conventional technique, the labeling index can be further increased, and a large amount of a target radioactive Zr complex can be generated. This is advantageous in that the production efficiency can be improved because the yield of the target radioactive Zr complex can be increased even in the case where the production scale is increased in the production on a commercial scale.

The additive having the above-described structure is considered to be a compound that reduces radiolysis in which radiation destroys the chemical structure of the ligand compound or the radioactive Zr complex or in which an unintended chemical reaction occurs. Therefore, the present inventors presume that by including such an additive in the reaction solution, the reaction of the present step proceeds well without radiolysis of the ligand compound and that the radioactive Zr complex as a product is also hardly decomposed even when the amount of radioactivity (amount of radioactivity prepared) at the start of the reaction used in the reaction is increased. This presumption is also supported by the fact that the labeling index is increased by increasing the content of the additive in the reaction solution as shown in examples described later.

In the present step, it is preferable to carry out the reaction by heating the reaction solution in a state where the pH of the reaction solution is in the acidic region. That is, in the present step, it is preferable to carry out the reaction in a state where the acidic state of the pH is maintained from the start to the end of the reaction. The fact that the pH of the reaction solution is in the acidic region means that the pH of the reaction solution is less than 7. By carrying out the reaction in a state where the pH of the reaction solution is in the acidic region, it is possible to appropriately maintain the functional group of the ligand compound that interacts with radioactive Zr, and/or radioactive Zr, in an ionic state and to maintain a state where it is easy to coordinate to each other in the reaction solution. As a result, the productivity of the radioactive Zr complex can be further increased.

More specifically, the present step is performed in a state where the pH of the reaction solution is preferably 2.0 or more and 6.0 or less, more preferably 3.0 or more and 5.0 or less.

The pH of the reaction solution is adjusted in advance so as to be in the acidic region before the reaction is started, that is, before the present step is performed, whereby the pH of the reaction solution can be maintained in the acidic region even during the present step.

The pH of the reaction solution can be adjusted, for example, by mixing an aqueous solution of the additive into the reaction solution. In addition, the pH of the reaction solution can be adjusted by preparing each of a radioactive Zr ion-containing solution, an aqueous solution of the ligand compound, and an aqueous solution of the additive in advance and mixing these aqueous solutions at an adjusted mixing ratio. Alternatively, the pH of the reaction solution can be adjusted by adding an inorganic acid such as hydrochloric acid or a metal hydroxide such as sodium hydroxide to a liquid in which the radioactive Zr ion, the ligand compound, and the additive are mixed.

From the viewpoint of further enhancing the labeling efficiency, the concentration of the additive in the reaction solution is preferably 0.1 mmol/L or more and 500 mmol/L or less, more preferably 1 mmol/L or more and 400 mmol/L or less, still more preferably 1 mmol/L or more and 300 mmol/L or less at the start of the present step. In addition, the concentration of the additive in the reaction solution is preferably higher than the radioactive Zr ion concentration and the ligand compound concentration in the reaction solution from the viewpoint of preventing radiolysis and further improving the labeling efficiency.

From the viewpoint of further increasing the yield of the target radioactive Zr complex, the concentrations of the ligand compounds in the reaction solution are each independently preferably 1 μmol/L or more and 100 μmol/L or less, more preferably 10 mol/L or more and 9,000 μmol/L or less, still more preferably 30 μmol/L or more and 600 mol/L or less, still more preferably 50 μmol/L or more and 500 μmol/L or less at the start of the present step.

As for the relationship between the additive and the pH of the reaction solution, in addition to using a compound of Formula (2) in which $R_{21}$ is —COOH, one or more and three or less groups among $R_{22}$ to $R_{26}$ are hydroxy groups, and the other groups are hydrogen atoms or a salt thereof, that is, hydroxybenzoic acid or a salt thereof, as the additive, it is preferable to perform the present step in a state where the pH of the reaction solution is preferably 2.0 or more and 6.0 or less, more preferably 3.0 or more and 5.0 or less. It is also preferable that the pH of the reaction solution is adjusted using the additive.

In the present embodiment, it is more preferable to use, as the additive, an additive having a structure represented by any one of Formulas (2a) to (2d) or a salt thereof, and it is still more preferable to use an additive having the structure represented by Formula (2b) or a salt thereof.

As for the relationship between the amount of the additive and the amount of radioactivity in the reaction solution, in addition to using as the additive a compound of Formula (2) in which $R_{21}$ is —COOH group, one or more and three or less groups among $R_{22}$ to $R_{26}$ are hydroxy groups, and the other groups are hydrogen atoms or a salt thereof, that is, hydroxybenzoic acid or a salt thereof, the lower limit of the content of the additive per unit amount of radioactivity (1 MBq) of the radioactive Zr ion in the reaction solution, that is, the ratio of the content of the additive to the amount of radioactivity (MBq) of the radioactive zirconium ion, is set to preferably 5 nmol/MBq or more, more preferably 20 nmol/MBq or more, at the start of the present step. The upper limit of the above ratio can be appropriately set in consideration of maintaining the pH of the reaction solution at a predetermined acidic condition and in consideration of the solubility of hydroxybenzoic acid or a salt thereof in the reaction solution.

By setting the ratio of the additive content per the amount of radioactivity to the above-mentioned predetermined range, the labeling efficiency can be further enhanced even in the case where the amount of radioactivity in the reaction solution is increased.

In the present embodiment, it is more preferable to use, as the additive, an additive having a structure represented by any one of Formulas (2a) to (2d) or a salt thereof, and it is still more preferable to use an additive having the structure represented by Formula (2b) or a salt thereof.

In particular, in the case where an additive of Formula (2) in which $R_{21}$ is —COOH, both of $R_{22}$ and $R_{25}$ are hydroxy groups, and all of $R_{23}$, $R_{24}$, and $R_{26}$ are hydrogen atoms or a salt thereof, that is, gentisic acid or a salt thereof, is used as the additive, the lower limit of the content of the additive per unit amount of radioactivity (1 MBq) of the radioactive Zr ion in the reaction solution, that is, the ratio of the content of the additive to the amount of radioactivity (MBq) of the radioactive zirconium ion, is set to preferably 5 nmol or more, more preferably 7 nmol or more, at the start of the present step. The upper limit of the ratio is preferably 125 nmol or less, more preferably 100 nmol or less, still more preferably 30 nmol or less, from the viewpoint of achieving both of maintaining the pH of the reaction solution at a predetermined acidic condition and sufficient solubility of gentisic acid in the reaction solution.

By appropriately controlling the content of gentisic acid on the basis of the amount of radioactivity of the radioactive Zr ion, the labeling efficiency can be further enhanced while maintaining the pH of the reaction solution in a desired range.

As for the relationship between the amount of the ligand compound and the amount of the additive in the reaction solution, in addition to using as the additive a compound of Formula (2) in which $R_{21}$ is —COOH, one or more and three or less groups among $R_{22}$ to $R_{26}$ are hydroxy groups, and the other groups are hydrogen atoms or a salt thereof, that is, hydroxybenzoic acid or a salt thereof, the ratio of the molar amount (nmol) of the additive in the reaction solution to the molar amount (nmol) of the ligand compound in the reaction solution is set to preferably 60 or more and 1,400 or less, more preferably 70 or more and 700 or less, still more preferably 250 or more and 500 or less, at the start of the present step.

By setting the molar ratio of the additive to the ligand compound within the above range, the labeling efficiency can be further enhanced while maintaining the pH of the reaction solution within a desired range.

In the present embodiment, it is more preferable to use, as the additive, an additive having a structure represented by any one of Formulas (2a) to (2d) or a salt thereof, and it is still more preferable to use an additive having the structure represented by Formula (2b) or a salt thereof.

In particular, in the case where an additive of Formula (2) in which $R_{21}$ is —COOH, both of $R_{22}$ and $R_{25}$ are hydroxy groups, and all of $R_{23}$, $R_{24}$, and $R_{26}$ are hydrogen atoms or a salt thereof, that is, gentisic acid or a salt thereof, is used as the additive, the ratio of the molar amount (nmol) of the additive in the reaction solution to the molar amount (nmol) of the ligand compound in the reaction solution is set to preferably 60 or more and 1,500 or less, more preferably 100 or more and 700 or less, still more preferably 300 or more and 500 or less, at the start of the present step.

The reaction solution used in the present step preferably further contains water and a water-soluble organic compound. The water-soluble organic compound in the present specification is a compound that exhibits a buffering action in a predetermined pH range but may not actually exhibit a buffering action in a complex-forming reaction solution, the compound being different from the above-described ligand compound and organic solvent. In addition, in the present specification, the reaction solution itself containing the water-soluble organic compound used in the present step may not exhibit a pH buffering action or may exhibit a pH buffering action depending on the pH of the entire reaction solution.

For example, such a water-soluble organic compound is one of acetic acid and salts thereof, phosphoric acid and salts thereof, 2-amino-2-(hydroxymethyl)propane-1,3-diol (Tris), 2-[4-(2-hydroxyethyl)-1-piperazinyl]ethanesulfonic acid (HEPES), and basic amino acids. Examples of the counter ion of the water-soluble organic compound include the various cations and anions described above. In addition, a neutral salt such as sodium chloride may be further added. These water-soluble organic compounds are also preferably selected according to the types and combination of the ligand compound and the additive.

Among them, as the water-soluble organic compound, acetic acid and a salt thereof, or HEPES is more preferably used, and acetic acid and a salt thereof are still more preferably used. That is, it is preferable to use an acetic acid-sodium acetate buffer solution or a HEPES buffer solution as an aqueous solution in which the water-soluble organic compound is dissolved in water, and it is preferable to use an acetic acid-sodium acetate buffer solution for the reaction solution.

From the viewpoint of suppressing an unintended pH change during the reaction and further increasing the labeling efficiency, the concentration of the water-soluble organic compound in the reaction solution is preferably 0.01 mol/L or more and 5.0 mol/L or less, more preferably 0.05 mol/L or more and 2.0 mol/L or less. For example, when acetic acid and a salt thereof are contained as the water-soluble organic compound, the concentration in the reaction solution is preferably 0.05 mol/L or more and 2.0 mol/L or less, more preferably 0.1 mol/L or more and 1 mol/L or less.

From the viewpoint of improving both the handleability of the ligand compound to be used and the stability of the resulting radioactive Zr complex, each of Rn, $R_{12}$, and $R_{13}$ is preferably a carboxyalkyl group represented by a $—(CH_2)_p$ COOH group, where p is an integer of 1 or more and 3 or less.

In this case, it is also preferable that one of $R_{14}$ and $R_{15}$ be a hydrogen atom or a carboxyalkyl group represented by a $—(CH_2)_pCOOH$ group, where p is an integer of 1 or more and 3 or less. In this case, it is also preferable that the other one of $R_{14}$ and $R_{15}$ is a carboxyalkyl group represented by a $—(CH_2)_pCOOH$ group, where p is an integer of 1 or more and 3 or less, or a reactive atomic group to be linked to the targeting agent or a group linked to the targeting agent.

In the case where $R_{11}$, $R_{12}$, $R_{13}$, $R_{14}$, and $R_{15}$ have the above-described suitable groups and where one of $R_{14}$ and $R_{15}$ is a hydrogen atom, the other of $R_{14}$ and $R_{15}$ is preferably a reactive atomic group to be linked to the targeting agent or a group linked to the targeting agent.

That is, in the case where $R_{14}$ is a reactive atomic group to be linked to the targeting agent or a group linked to the targeting agent, $R_{15}$ is preferably a hydrogen atom, and in the case where $R_{15}$ is a reactive atomic group to be linked to the targeting agent or a group linked to the targeting agent, $R_{14}$ is preferably a hydrogen atom.

In the case where a ligand compound containing a group linked to the targeting agent in Formula (1) is used, the targeting agent is preferably one kind or two or more kinds among atomic groups including those selected from the group consisting of chain peptides, cyclic peptides, or combinations thereof, proteins, antibodies or fragments thereof, peptide aptamers, growth factors, Affibody, UniBody, Nanobody, monosaccharides, polysaccharides, vitamins, antisense nucleic acids, siRNAs, miRNAs, nucleic acid aptamers, decoy nucleic acids, cPG oligonucleic acids, peptide nucleic acids, liposomes, micelles, carbon nanotubes, and nanoparticles.

The “targeting agent” in the present specification refers to a chemical structure that gives rise to directionality to a target organ or tissue in a living body or specificity to a target molecule. In the present specification, a target organ or tissue and a target molecule are also collectively referred to as a “target site”.

These targeting agents may be directly bonded to the ligand compound or indirectly bonded through other known linker structures such as PEG.

In addition, these targeting agents may be configured to be capable of being linked to the ligand compound using a modified reactive atomic group that can be bonded to another structure. In order to achieve the linkage to the ligand compound, for example, a known reaction such as a click reaction can be employed.

In the case where a click reaction is used for linking, for example, both the reactive atomic group of the targeting agent and the reactive atomic group of the ligand compound to be linked to the targeting agent can be groups containing click-reactive atomic groups.

By using the ligand compound having such a chemical structure, it is possible to easily achieve bonding to the targeting agent having specificity or directionality to a target site, and it is possible to obtain the radioactive Zr complex having specificity or directionality to the target site with high yield in a state where the specificity or directionality to the target site of the targeting agent is sufficiently maintained.

In the case where the targeting agent includes a peptide, the atomic group preferably includes a chain peptide, a cyclic peptide, or a combination thereof, a protein, or an antibody or a fragment thereof that is specifically bonded to a specific molecule.

Examples of such an atomic group include peptides having three or more constituent amino acid residues, such as antibodies (immunoglobulins) of the IgG, IgA, IgM, IgD, and IgE classes, antibody fragments such as Fab fragments and F(ab')2 fragments, and peptide aptamers. In addition, an amino acid constituting such a targeting agent may be natural or synthetic.

The molecular weight of the above atomic group including a peptide is not particularly limited.

Various peptides that can be used as the targeting agent can be synthesized by conventionally known methods, such as techniques such as a liquid phase synthesis method, a solid phase synthesis method, an automated peptide synthesis method, a gene recombination method, a phage display method, genetic code reprogramming, and a random non-standard peptide integrated discovery (RaPID) method. In the synthesis of various peptides, functional groups of amino acids to be used may be protected as necessary.

In the case where the targeting moiety is an atomic group containing a nucleic acid, the atomic group is preferably an atomic group containing an antisense nucleic acid, siRNA, miRNA, nucleic acid aptamer, decoy nucleic acid, cPG oligo-nucleic acid, or peptide nucleic acid that is specifically bonded to a specific molecule. In addition, the nucleobase constituting such a targeting agent may be natural ones, such as a deoxyribonucleic acid and a ribonucleic acid, or synthetic ones.

The atomic group containing the above-described nucleic acid that can be used in the present invention can be produced by a conventionally known method. For example, in the case of a nucleic acid aptamer, a nucleic acid aptamer that is specifically bonded to a specific target substance such as a protein can be produced using systematic evolution of ligands by exponential enrichment (SELEX).

In the case where a ligand compound containing a click-reactive atomic group is used as the ligand compound containing a reactive atomic group to be linked to the targeting agent used in the present invention, a click-reactive atomic group derived from a known reagent that can be used for a click reaction can be appropriately used.

The "reactive atomic group" in the present specification refers to a chemical structure that directly undergoes a reaction for bonding one compound to the other compound. Examples of such a reactive atomic group include, but are not limited to, click-reactive atomic groups.

From the viewpoint of simplifying the reaction process, the click-reactive atomic group as the reactive atomic group is preferably an atomic group that can be used for a metal-catalyst-free click reaction, and examples thereof include an alkynyl group, an azido group, and a diene or a dienophile such as 1,2,4,5-tetrazine and an alkenyl group.

The click reaction is a reaction of a combination of an alkyne and an azide or a combination of a diene and a dienophile, such as 1,2,4,5-tetrazine and an alkene. Specific examples of the click reaction of such a combination of atomic groups include a Huisgen cycloaddition reaction and an inverse electron demand Diels-Alder reaction.

Typically, the chemical structure produced by the click reaction of the combination of an alkyne and an azide contains a triazole skeleton, and the chemical structure produced by the click reaction of the combination of 1,2,4,5-tetrazine and an alkene as the combination of a diene and a dienophile contains a pyridazine skeleton. Therefore, a triazole skeleton can be formed by a click reaction in the case where the click-reactive atomic group that can be contained in the reactive atomic group to be linked to the targeting agent is an atomic group containing an alkyne or an azide. Alternatively, a pyridazine skeleton can be formed by a click reaction in the case where the click-reactive atomic group that can be contained in the reactive atomic group to be linked to the targeting agent is an atomic group containing 1,2,4,5-tetrazine or an alkene as a diene or a dienophile.

Specific examples of the click-reactive atomic group include an atomic group containing dibenzylcyclooctyne (DBCO) as an alkyne (Formula (5a)), an atomic group containing an azido group as an azide (Formula (5b)), an atomic group containing 1,2,4,5-tetrazine (Formula (5c)), and an atomic group containing trans-cyclooctene (TCO) as an alkene (Formula (5d)) as shown in the following formulas.

(5a)

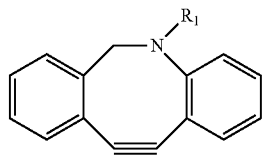

Dibenzylcyclooctyne (5b)

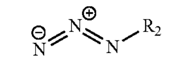

Azide (5c)

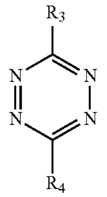

1,2,4,5-tetrazine (5d)

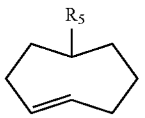

trans-cyclooctene

In Formula (5a), $R_1$ represents a bonding site to an atomic group including the ligand compound or the targeting agent.

In Formula (5b), $R_2$ represents a bonding site to an atomic group including the ligand compound or the targeting agent.

In Formula (5c), one of $R_3$ and $R_4$ represents a bonding site to an atomic group including the ligand compound or the targeting agent, and the other represents a hydrogen atom, a methyl group, a phenyl group, or a pyridyl group.

In Formula (5d), $R_5$ represents a bonding site to an atomic group including the ligand compound or the targeting agent.

In the case where a click-reactive atomic group is introduced into the ligand compound, it can be introduced using various commercially available reagents. Specifically, in the case where an atomic group containing dibenzylcyclooctyne (DBCO) is introduced as the click-reactive atomic group, for example, DBCO reagents such as DBCO-C6-Acid, DBCO-Amine, DBCO-Maleimide, DBCO-PEG acid, DBCO-PEG-NHS ester, DBCO-PEG-Alcohol, DBCO-PEG-amine, DBCO-PEG-NH-Boc, Carboxyrhodamine-PEG-DBCO, Sulforhodamine-PEG-DBCO, TAMRA-PEG-DBCO, DBCO-PEG-Biotin, DBCO-PEG-DBCO, DBCO-PEG-Maleimide, TCO-PEG-DBCO, and DBCO-mPEG can be used.

As a suitable ligand compound used in the present invention, for example, a ligand compound having a structure represented by any of following Formulas (1-a) to (1-e) can be used, but the ligand compound is not limited thereto. Even with the ligand compound having any structure, the effect of stably improving the labeling index is sufficiently exhibited. In each of the following formulas, P represents an atomic group containing a reactive atomic group or an atomic group containing the targeting agent. From the viewpoint of stably improving the labeling index, a ligand compound having a structure represented by above Formula (1-b), (1-d), or (1-e) is more preferably used.

(1-a)

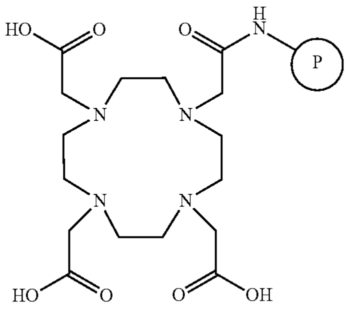

(1-b)

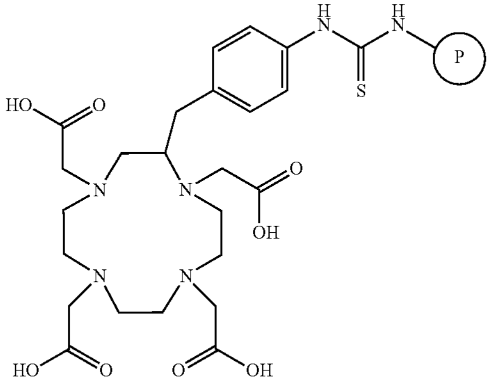

-continued (1-c)

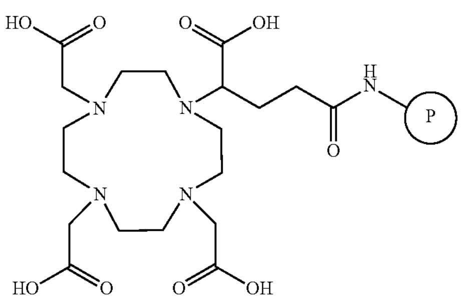

(1-d)

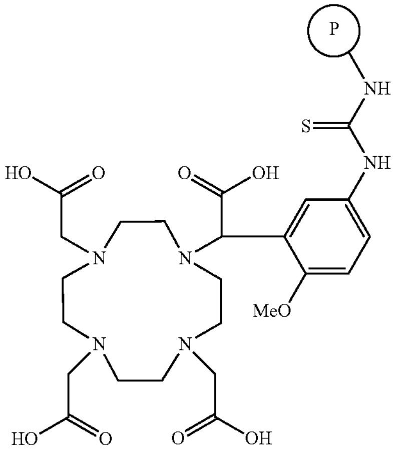

(1-e)

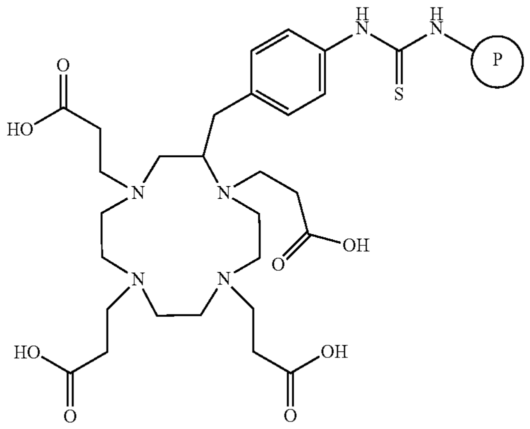

In the case where a ligand compound of Formula (1) containing a click-reactive atomic group is used, it is also preferable that the ligand compound and the click-reactive atomic group are indirectly bonded by a linker structure represented by following Formula (P). The structure is a structure derived from ethylene glycol, and in Formula (P), n is preferably an integer of 2 or more and 10 or less, more preferably an integer of 2 or more and 8 or less.

(P)

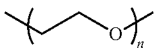

The structure of the ligand compound containing a click-reactive atomic group is not particularly limited as long as the effect of the present invention is exhibited, but it is more preferable to have the following structure. That is, the ligand compound more preferably contains at least one of DO3A-DBCO, DOTA-DBCO, DO3A-PEG4-DBCO, DO4A-PEG7-Tz, and DOTAGA-DBCO shown below.

(X)

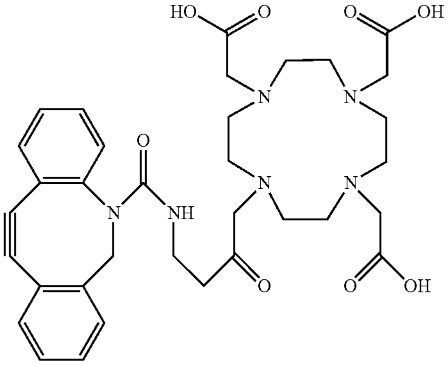

DO3A-DBCO

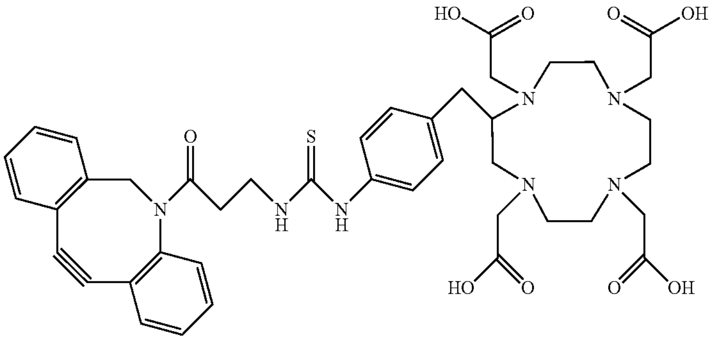

DOTA-DBCO

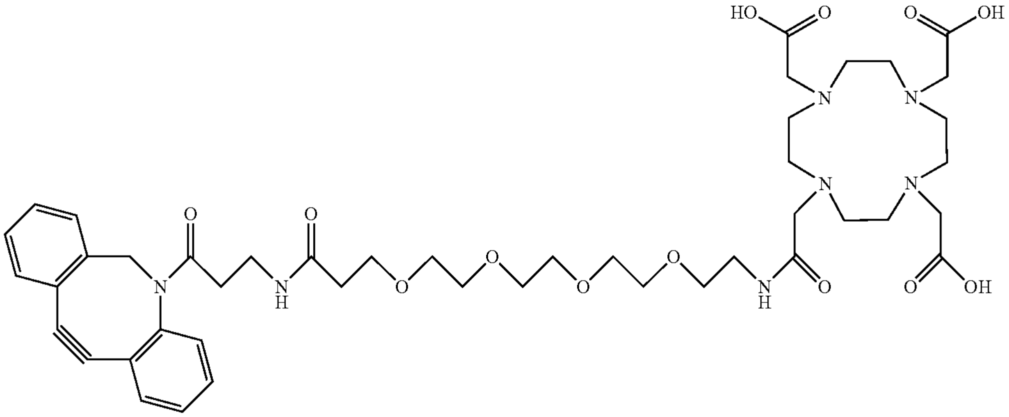

DO3A-PEG4-DBCO

-continued

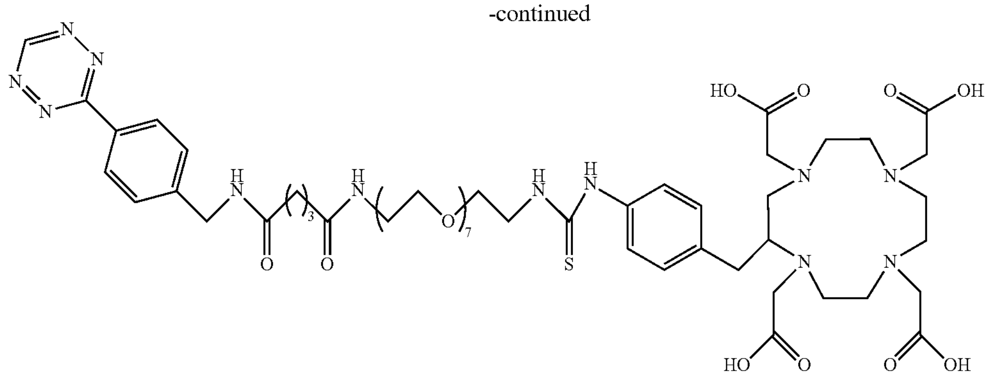

DO4A-PEG7-Tz

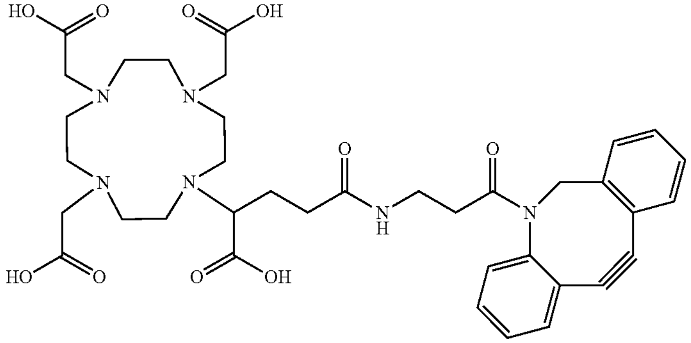

DOTAGA-DBCO

In the case where a ligand compound containing a click-reactive atomic group as the reactive atomic group is used, for example, a radioactive Zr ion is coordinated to the ligand compound by the above-described method, and then a click reaction or the like of the click-reactive atomic group of the ligand compound to which the radioactive Zr ion has been coordinated and the click-reactive atomic group of the targeting agent is carried out, whereby a radioactive Zr complex can be produced.

In this case, as the targeting agent, a compound modified with a click-reactive atomic group that is specifically bonded to a reactive atomic group in the ligand compound can be used.

As the click-reactive atomic group for modifying the targeting agent, the same group as those described above can be used. By using such a compound, a radioactive Zr complex having specificity or directionality to the target site can be produced.

The radioactive Zr complex generated through the above-described steps exists in a state of being dissolved in the reaction solution. That is, the radioactive Zr complex can be obtained as an aqueous liquid. The aqueous liquid containing the radioactive Zr complex may be used as it is or may be purified using a filtration filter, a membrane filter, a column filled with various fillers, chromatography, or the like.

Examples of the step after the radioactive Zr complex is obtained include a formulation step for obtaining a radioactive drug containing the radioactive Zr complex as an active ingredient. The formulation step can be performed by appropriately adding various additives such as a pH adjusting agent such as a citrate buffer solution, a phosphate buffer solution, and a borate buffer solution, a solubilizing agent such as polysorbate, a stabilizer, and an antioxidant, or by adjusting the radioactivity concentration by dilution with water or an isotonic solution such as physiological saline. In addition, the formulation step may include a step of adding various additives or adjusting the concentration and then performing sterilizing filtration with a membrane filter or the like to prepare an injection.

Examples of a substituent that can be substituted for $R_{28}$ in Formula (2) above include a halogen atom, a saturated or unsaturated alkyl group, a hydroxy group, an aldehyde group, a carboxy group, an acyl group, an amino group, a nitro group, an ester group, an isothiocyanate group, a thioxy group, a cyano group, an amide group, an imide group, a phosphate group, a phenyl group, a benzyl group, and a pyridyl group. One of these substituents may be substituted alone, or a combination of two or more of these substituents may be substituted.

EXAMPLES

Hereinafter, the present invention will be described in more detail with reference to examples. However, the scope of the present invention is not limited to such examples. The following examples were all carried out at atmospheric pressure. In Table 1, a field indicated by "-" indicates that it is not contained.

Example 1 and Comparative Example 1

$^{89}Zr$ was used as the radioactive Zr element. DOTA (in Formula (1) above, $R_{11}$, $R_{12}$, $R_{13}$, and $R_{14}$ are all "—$CH_2COOH$" groups, and $R_{15}$ is a hydrogen atom) was used as the ligand compound.

The above ligand compound was dissolved in water for injection to prepare an aqueous solution containing 10 mmol/L of the above ligand compound.

In a reaction vessel (glass vial), 7.5 μL of the aqueous solution of the ligand compound, 25 μL of a $^{89}Zr$ ion-containing solution (solvent: 0.1 mol/L hydrochloric acid aqueous solution, radioactivity concentration: 3.4 GBq/mL, specific activity: 11.4 MBq/nmol) as the radioactive Zr source, and 12.5 μL of a 0.13 mol/L acetic acid-sodium acetate buffer (pH: 5.5) as a buffer-containing aqueous solution were mixed.

In Example 1, a 300 mmol/L aqueous solution obtained by dissolving gentisic acid (Formula (2b) above) as the additive in water for injection was further added so as to achieve a final concentration shown in Table 1 below.

In Comparative Example 1, gentisic acid was not added.

In this way, reaction solutions having various concentrations and pH values shown in Table 1 below were prepared. All of these reaction solutions did not contain an organic solvent.

Then, while the pH of each reaction solution was maintained, the reaction solution was heated at a heating temperature of 70° C. and a heating time of 1 hour to provide a solution containing a $^{89}Zr$ complex as a radioactive Zr-labeled compound.

Using thin-layer chromatography (manufactured by Agilent Technologies, Inc., model number: iTLC-SG, developing solvent: water/acetonitrile (1:1)), 2 μL of the obtained $^{89}Zr$ complex solution was developed at a development distance of 10 cm.

The thin-layer chromatogram after development was introduced into a TLC analyzer (GITA Star), and the total $^{89}Zr$ radioactivity count including unreacted $^{89}Zr$ and the radioactivity count of the $^{89}Zr$ complex in the $^{89}Zr$ complex solution were each measured. Then, the percentage of the radioactivity count of the $^{89}Zr$ complex relative to the total $^{89}Zr$ radioactivity count was calculated as the labeling index (%). The labeling index indicates the degree of progress of the labeling reaction, and a higher labeling index means that a larger amount of the target radioactive Zr-labeled compound is generated and that the labeling reaction is progressing well. The results are shown in Table 1 below.

Example 2 and Comparative Example 2

In the present examples, a ligand compound obtained by bonding p-SCN-Bn-DOTA and physalaemin (molecular weight: 1,265 Da) as the chain peptide by a conventional method was used as the ligand compound. This ligand compound is a form included in Formula (1-b) above. Details of the chemical structure of this ligand compound are shown in following Formula (E1).

In Example 2, a 300 mmol/L aqueous solution obtained by dissolving gentisic acid (Formula (2b) above) as the additive in water for injection was further added so as to achieve a final concentration shown in Table 1 below.

In Comparative Example 2, gentisic acid was not added.

In this way, reaction solutions having various concentrations and pH values shown in Table 1 below were prepared. Each of the reaction solutions of Example 2 and Comparative Example 2 contained DMSO as the organic solvent at a final concentration of 50 vol %.

The operation and evaluation were performed in the same manner as in Example 1 except for this point. The results are shown in Table 1 below.

Examples 3 to 7 and Comparative Examples 3 and 4

In the present examples, a ligand compound obtained by bonding p-SCN-Bn-DOTA and daptomycin (molecular weight: 1,619 Da) as the cyclic peptide by a conventional method was used as the ligand compound. This ligand compound is a form included in Formula (1-b) above. Details of the chemical structure of this ligand compound are shown in following Formula (E2).

In Examples 3 to 7, a 300 mmol/L aqueous solution obtained by dissolving gentisic acid (Formula (2b) above) as the additive in water for injection was further added so as to achieve final concentrations in the reaction solutions shown in Table 1 below.

In both of Comparative Examples 3 and 4, gentisic acid was not added.

In this way, reaction solutions having various concentrations and pH values shown in Table 1 below were prepared. Each of the reaction solutions of Examples 3 to 7 and Comparative Examples 3 and 4 contained DMSO as the organic solvent at a final concentration of 50 vol %.

The operation and evaluation were performed in the same manner as in Example 1 except for this point. The results are shown in Table 1 below.

Example 8

The operation and evaluation were carried out in the same manner as in Example 1 except that adjustment was made such that the concentration of gentisic acid in the reaction solution was the concentration shown in Table 1 below and that DMSO was contained at a final concentration of 50 vol %. The results are shown in Table 1.

Example 9

The operation and evaluation were carried out in the same manner as in Example 1 except that salicylic acid (Formula (2a) above) was used as the additive and that preparation was performed such that the concentration of salicylic acid in the reaction solution was the concentration shown in Table 1 below and that DMSO was contained at a final concentration of 50 vol %. The results are shown in Table 1.

Example 10

The operation and evaluation were carried out in the same manner as in Example 1 except that protocatechuic acid (Formula (2c) above) was used as the additive and that preparation was performed such that the concentration of protocatechuic acid in the reaction solution was the concentration shown in Table 1 below and that DMSO was contained at a final concentration of 50 vol %. The results are shown in Table 1.

Example 11

DOTAGA-DBCO (Formula (X) above) as the ligand compound was dissolved in a 0.156 mol/L acetic acid-sodium acetate buffer (pH: 5.5) to prepare a solution containing 0.3 mmol/L of the ligand compound.

In a reaction vessel (glass vial), 128.9 μL of the above ligand compound solution and 85.9 μL of a $^{89}Zr$ ion-containing solution (solvent: 0.1 mol/L hydrochloric acid aqueous solution, radioactivity concentration: 8.0 GBq/mL, specific activity: 25.4 MBq/nmol) as the radioactive Zr source were mixed.

In Example 11, a 150 mmol/L solution obtained by dissolving gentisic acid as the additive in a 0.156 mol/L acetic acid-sodium acetate buffer (pH: 5.5) was further added so as to achieve a final concentration shown in Table 1 below.

The operation and evaluation were performed in the same manner as in Example 1 except for this point. The results are shown in Table 1.

(E1)
DOTA-Physalemine
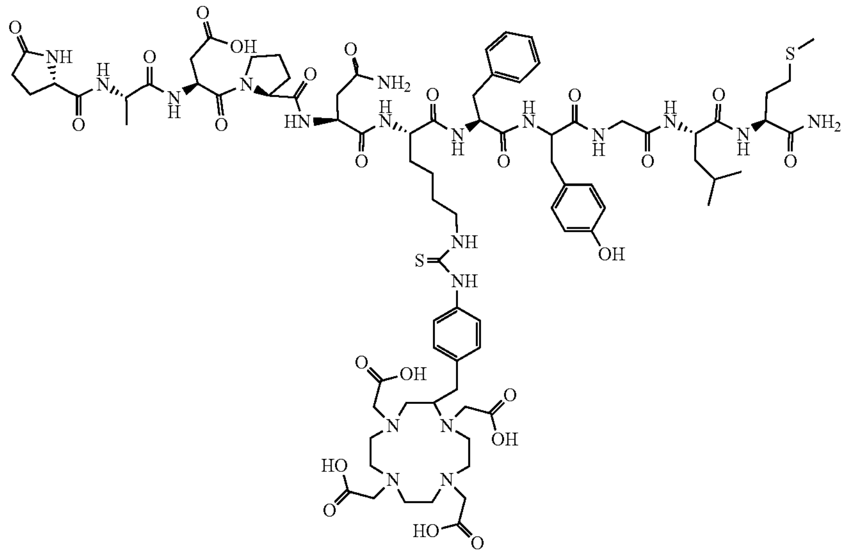
Chemical Formula : $C_{82}H_{117}N_{19}O_{24}S_2$
Exact Mass: 1815.80
Molecular Weight: 1817.07
(E2)
DOTA-Daptomycin
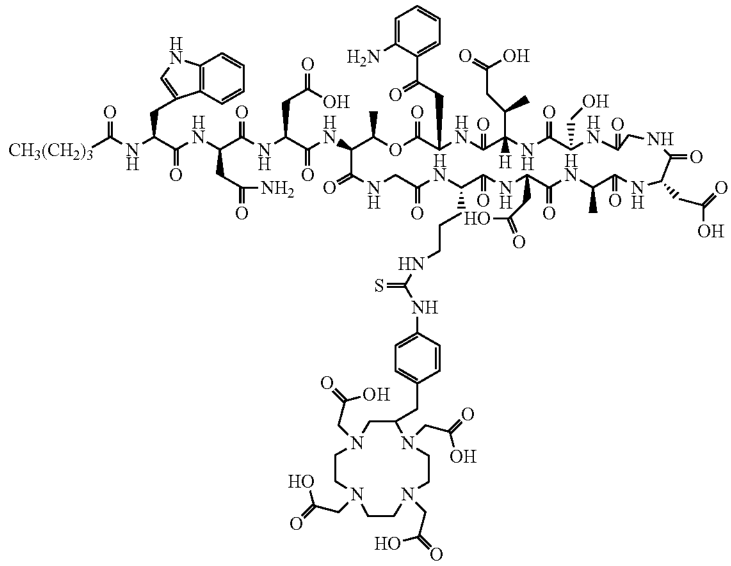
Chemical Formula : $C_{96}H_{134}N_{22}O_{34}S$
Exact Mass: 2170.92
Molecular Weight: 2172.31

TABLE 1

| | Composition of reaction solution | | | | | | | |
|---|---|---|---|---|---|---|---|---|
| | Ligand compound | | | Radioactive Zr | | | Additive | |
| | Type | Concentration [μmol/L] | Molar amount A [nmol] | Amount of radioactivity at start B [MBq] | Zr ion concentration [nmol/L] | Zr ion amount [nmol] | Type | Concentration [mmol/L] |
| Comp. Ex. 1 | DOTA | 100 | 7.5 | 85.7 | 772.9 | 0.058 | — | — |
| Example 1 | | 100 | 7.5 | 84.9 | 765.7 | 0.057 | Gentisic acid | 8.5 |
| Comp. Ex. 2 | DOTA- | 100 | 7.5 | 85.2 | 768.4 | 0.058 | — | — |
| Example 2 | physalaemin | 100 | 7.5 | 73.5 | 662.9 | 0.050 | Gentisic acid | 7.4 |
| Comp. Ex. 3 | DOTA- | 100 | 7.5 | 75.7 | 682.7 | 0.051 | — | — |
| Comp. Ex. 4 | daptomycin | 100 | 7.5 | 96.3 | 868.5 | 0.065 | — | — |
| Example 3 | | 100 | 7.5 | 69.3 | 625.0 | 0.047 | Gentisic acid | 6.9 |
| Example 4 | | 100 | 7.5 | 95.3 | 859.5 | 0.064 | Gentisic acid | 10 |
| Example 5 | | 100 | 7.5 | 171.2 | 1544.0 | 0.116 | Gentisic acid | 17.1 |
| Example 6 | | 100 | 7.5 | 93.7 | 845.0 | 0.063 | Gentisic acid | 30 |
| Example 7 | | 100 | 7.5 | 170.9 | 1541.3 | 0.116 | Gentisic acid | 50 |
| Example 8 | DOTA- | 100 | 7.5 | 93.7 | 845.0 | 0.063 | Gentisic acid | 28.8 |
| Example 9 | daptomycin | 100 | 7.5 | 122.0 | 1100.3 | 0.083 | Salicylic acid | 138.4 |
| Example 10 | | 100 | 7.5 | 101.4 | 914.5 | 0.069 | Protocatechuic acid | 69.2 |
| Example 11 | DOTAGA-DBCO | 129 | 27.09 | 689.0 | 1549.8 | 0.466 | Gentisic acid | 42.9 |

| | Composition of reaction solution | | | | | | | | |
|---|---|---|---|---|---|---|---|---|---|
| | Additive Molar amount | Water-soluble organic compound | | | | | C/B ratio | B/A ratio | Labeling index of radioactive Zr |
| | C [nmol] | Type | Concentration [mol/L] | DMSO | pH | C/A ratio | [nmol/MBq] | [MBq/nmol] | complex [%] |
| Comp. Ex. 1 | — | Acetic | 0.13 | Absent | 5.50 | — | — | 11.4 | 0 |
| Example 1 | 637.5 | acid-Na | | | 4.00 | 85 | 7.5 | 11.3 | 54 |
| Comp. Ex. 2 | — | acetate | | Present | 6.00 | — | — | 11.4 | 0 |
| Example 2 | 555 | | | | 5.50 | 74 | 7.6 | 9.8 | 53 |
| Comp. Ex. 3 | — | | | | 6.00 | — | — | 10.1 | 33 |
| Comp. Ex. 4 | — | | | | 6.00 | — | — | 12.8 | 0 |
| Example 3 | 517.5 | | | | 5.50 | 69 | 7.5 | 9.2 | 56 |
| Example 4 | 750 | | | | 5.50 | 100 | 7.9 | 12.7 | 54 |
| Example 5 | 1282.5 | | | | 5.20 | 171 | 7.5 | 22.8 | 54 |
| Example 6 | 2250 | | | | 5.20 | 300 | 24.0 | 12.5 | 70 |
| Example 7 | 3750 | | | | 5.00 | 500 | 21.9 | 22.8 | 75 |
| Example 8 | 2163 | | | | 5.18 | 288.4 | 23.1 | 12.5 | 70 |
| Example 9 | 10377 | | | | 5.27 | 1383.6 | 85.1 | 16.3 | 72 |
| Example 10 | 5190 | | | | 4.98 | 692 | 51.2 | 13.5 | 96 |
| Example 11 | 12885 | | 0.11 | Absent | 4.00 | 475.6 | 18.7 | 25.4 | 97 |

As described above, it is found that in the production method of the examples in which a reaction solution containing an additive having a specific structure is heated to cause the reaction, the labeling reaction proceeds well even in a state where the amount of radioactivity at the start of the reaction is high, and a high labeling index can be achieved in the reaction of Zr ions with a ligand compound containing DOTA or a DOTA derivative, as compared with the production method of the comparative examples. In addition, it is also found that a high labeling index can be achieved in the production method of each example in which the reaction is performed by heating with the pH of the reaction solution in a suitable acidic region. In particular, in Examples 6 to 10 in which the content of the additive in the reaction solution was increased, it was possible to further increase the labeling index of Zr.

Although not shown in the table, gentisic acid was dissolved to a concentration of 900 mmol/L in a 0.78 mol/L acetic acid-sodium acetate buffer solution (pH 5.5) at 25° C., and the pH was 3.59. Salicylic acid was dissolved in the same buffer solution to a concentration of 500 mmol/L, and the pH was 4.36. Protocatechuic acid was dissolved in the same buffer solution to a concentration of 400 mmol/L, and the pH was 4.77.

The present inventors have also confirmed that when these buffer solutions are used as reaction solutions, the labeling index to DOTA as measured by thin-layer chromatography is 50% or more. In addition, the use of an acid as the additive is advantageous in that the pH of the reaction solution can be adjusted and a predetermined amount of the additive can be added in one step, and the labeling index can be improved.

As described above, the present invention provides a production method that can realize a high labeling index in a reaction of a radioactive zirconium ion with a ligand compound containing DOTA or a DOTA derivative.

The invention claimed is:

1. A method for producing a radioactive zirconium complex, the method comprising combining a radioactive zirconium ion and a ligand compound and an additive or salt thereof in a reaction solution, and heating the reaction solution to 50° C. or higher and 80° C. or lower to form a radioactive zirconium complex, wherein the reaction solution has:

an amount of radioactivity of the radioactive zirconium ion of 60 MBq or more at a start of the reaction; and an amount of radioactivity of the radioactive zirconium ion of 5 MBq or more per 1 nmol of the ligand compound at the start of the reaction, wherein the ligand compound is represented by formula (1)

(1)

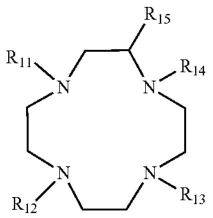

wherein $R_{11}$, $R_{12}$, and $R_{13}$ each independently represent a $—(CH_2)_pCOOH$ group, a $—(CH_2)_pC_5H_4N$ group, a $—(CH_2)_pPO_3H_2$ group, or a $—(CH2)_pCONH_2$ group, one of $R_{14}$ and $R_{15}$ represents a hydrogen atom, a $—(CH_2)_p$ COOH group, a $—(CH_2)_pC_5H_4N$ group, a $—(CH_2)_pPO_3H_2$ group, a $—(CH_2)_pCONH_2$ group, or a $—(CHCOOH)(CH_2)_nCOOH$ group, and the other of $R_{14}$ or $R_{15}$ is a $—(CH_2)_pCOOH$ group, a $—(CH_2)_p$ $C_5H_4N$ group, a $—(CH_2)_pPO_3H_2$ group, a $—(CH_2)_p$ $CONH_2$ group, a reactive atomic group to be linked to a targeting agent, or a group linked to the targeting agent, and p each independently represents an integer of 0 or more and 3 or less;

wherein the additive is either represented by formula (2) or is a salt of the compound represented by formula (2)

(2)

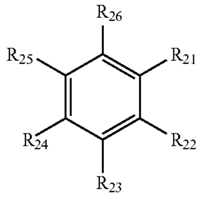

wherein $R_{21}$ represents a $—COOH$ group, a $—CH_2COOH$ group, a $—CH_2OH$ group, a $—COOR_{28}$ group, a $—CONH_2$, group or a $—CONHR_{28}$ group, 1 or more and 3 or less groups of $R_{22}$ to $R_{26}$ represent hydroxy groups, and the remaining groups represent hydrogen atoms, and $R_{28}$ represents a substituted or unsubstituted alkyl, a substituted or unsubstituted aryl, or a substituted or unsubstituted alkylaryl, and wherein the additive reduces decomposition caused by the radioactivity of the radioactive zirconium ion and/or the radioactive zirconium complex.

2. The method for producing a radioactive zirconium complex according to claim 1, wherein the pH of the reaction solution is in an acidic region.

3. The method for producing a radioactive zirconium complex according to claim 2, wherein the pH of the reaction solution is 2.0 or more and 6.0 or less.

4. The method for producing a radioactive zirconium complex according to claim 3, wherein, in formula (2) $R_{21}$ is a $—COOH$ group, one or more and three or less groups among $R_{22}$ to $R_{26}$ are hydroxy groups, and the remaining groups among $R_{22}$ to $R_{26}$ are hydrogen atoms.

5. The method for producing a radioactive zirconium complex according to claim 1, wherein, in formula (2) $R_{21}$ is a $—COOH$ group, one or more and three or less groups among $R_{22}$ to $R_{26}$ are hydroxy groups, and the remaining groups among $R_{22}$ to $R_{26}$ are hydrogen atoms, and a ratio of a content of the additive to the amount of radioactivity (MBq) of the radioactive zirconium ion at the start of the reaction is 5 nmol/MBq or more.

6. The method for producing a radioactive zirconium complex according to claim 1, wherein, in formula 2 $R_{21}$ is a $—COOH$ group, both of $R_{22}$ and $R_{25}$ are hydroxy groups, and all of $R_{23}$, $R_{24}$, and $R_{26}$ are hydrogen atoms, and a ratio of a content of the additive to the amount of radioactivity (MBq) of the radioactive zirconium ion at the start of the reaction is 5 nmol/MBq or more and 125 nmol/MBq or less.

7. The method for producing a radioactive zirconium complex according to claim 1, wherein, in formula 2 $R_{21}$ is a $—COOH$ group, both of $R_{22}$ and $R_{25}$ are hydroxy groups, and all of $R_{23}$, $R_{24}$, and $R_{26}$ are hydrogen atoms, and a ratio of a molar amount (nmol) of the additive to a molar amount (nmol) of the ligand compound is 60 or more and 1,500 or less.

8. The method for producing a radioactive zirconium complex according to claim 1, wherein the reaction solution further contains water and a water-soluble organic compound, and the water-soluble organic compound includes at least one of acetic acid and a salt thereof, phosphoric acid and a salt thereof, 2-amino-2-(hydroxymethyl)propane-1,3-diol, 2-[4-(2-hydroxyethyl)-1-piperazinyl)ethanesulfonic acid, tetramethylammonium acetate, and a basic amino acid.

9. The method for producing a radioactive zirconium complex according to claim 8, wherein a concentration of the water-soluble organic compound contained in the reaction solution is 0.01 mol/L or more and 5.0 mol/L or less.

10. The method for producing a radioactive zirconium complex according to claim 8, wherein the reaction solution contains acetic acid and a salt thereof as the water-soluble organic compound.

11. The method for producing a radioactive zirconium complex according to claim 1, wherein in Formula (1) above, all of $R_{11}$, $R_{12}$, and $R_{13}$ represent $—(CH_2)_pCOOH$ groups, one of $R_{14}$ and $R_{15}$ represents a hydrogen atom or a $—(CH_2)_pCOOH$ group, the other of $R_{14}$ and $R_{15}$ represents either a $—(CH_2)_p$ COOH group, the reactive atomic group to be linked to the targeting agent, or the group linked to the targeting agent, $R_{15}$ represents a hydrogen atom in a case where $R_{14}$ represents the reactive atomic group to be linked to the targeting agent or the group linked to the targeting agent, and $R_{14}$ represents a hydrogen atom in a case where $R_{15}$ represents the reactive atomic group to be linked to the targeting agent or the group linked to the targeting agent.

12. The method for producing a radioactive zirconium complex according to claim 1, wherein the targeting agent in Formula (1) above is present and includes an atomic group containing one or two or more selected from the group consisting of a chain peptide, a cyclic peptide, or a combination thereof, a protein, an antibody or a fragment thereof, a growth factor, a monosaccharide, a polysaccharide, a vitamin, an antisense nucleic acid, a siRNA, a miRNA, a nucleic acid aptamer, a decoy nucleic acid, a CpG oligonucleic acid, a peptide nucleic acid, a liposome, a micelle, a carbon nanotube, and a nanoparticle.

13. The method for producing a radioactive zirconium complex according to claim 11, wherein in Formula (1) above, either the reactive atomic group to be linked to the targeting agent is present and includes a click-reactive group selected from an azido group, an alkynyl group, a diene or a dienophile, or the group linked to the targeting agent is present and includes a chemical structure produced by the click reaction or a triazole group.

14. The method for producing a radioactive zirconium complex according to claim 1, wherein the radioactive zirconium ion is coordinated to the ligand compound using the ligand compound having the reactive atomic group to be linked to the targeting agent in Formula (1) above, and the reactive atomic group is then reacted with the targeting agent.

* * * * *